United States Patent
Mueller et al.

(10) Patent No.: US 10,111,508 B2
(45) Date of Patent: *Oct. 30, 2018

(54) COMPOSITION AND METHOD FOR TREATING KERATIN FIBERS WITH FLASH EVAPORATION

(71) Applicant: Henkel AG & Co. KGaA, Duesseldorf (DE)

(72) Inventors: Burkhard Mueller, Duesseldorf (DE); Thorsten Knappe, Schenefeld (DE)

(73) Assignee: Henkel AG & Co. KGaA (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/619,378

(22) Filed: Jun. 9, 2017

(65) Prior Publication Data

US 2017/0273424 A1 Sep. 28, 2017

Related U.S. Application Data

(63) Continuation of application No. PCT/EP2015/076538, filed on Nov. 13, 2015.

(30) Foreign Application Priority Data

Dec. 11, 2014 (DE) .......................... 10 2014 225 554

(51) Int. Cl.
| | |
|---|---|
| *A45D 19/16* | (2006.01) |
| *A61K 8/34* | (2006.01) |
| *A61Q 5/10* | (2006.01) |
| *A61Q 5/06* | (2006.01) |
| *B01B 1/00* | (2006.01) |

(52) U.S. Cl.
CPC ................ *A45D 19/16* (2013.01); *A61K 8/34* (2013.01); *A61Q 5/06* (2013.01); *A61Q 5/10* (2013.01); *B01B 1/005* (2013.01); *A61K 2800/4324* (2013.01); *A61K 2800/5426* (2013.01); *A61K 2800/805* (2013.01); *A61K 2800/87* (2013.01)

(58) Field of Classification Search
CPC . A45D 19/16; A61Q 5/06; A61K 8/34; A61K 2800/805; A61K 2800/4324

See application file for complete search history.

(56) References Cited

U.S. PATENT DOCUMENTS

| | | | |
|---|---|---|---|
| 3,167,478 A | | 1/1965 | Charle et al. |
| 5,723,433 A | | 3/1998 | Duvall et al. |
| 2013/0018333 A1* | | 1/2013 | Thomason .......... A61M 35/003 604/290 |
| 2013/0205515 A1* | | 8/2013 | Misu ...................... A61K 8/411 8/401 |

FOREIGN PATENT DOCUMENTS

| | | |
|---|---|---|
| GB | 2207443 A | 2/1989 |
| WO | 200183071 | 11/2001 |

OTHER PUBLICATIONS

PCT International Search Report (PCT/EP2015/076538) dated Dec. 23, 2015.

* cited by examiner

*Primary Examiner* — Eisa B Elhilo
(74) *Attorney, Agent, or Firm* — James J. Cummings

(57) ABSTRACT

A cosmetic product includes a cosmetic preparation including, relative to the total weight thereof, 50 to 90 wt. % polar solvent, and 0.001 to 10 wt. % direct dye. The product also includes a device for flash evaporation of the cosmetic preparation.

20 Claims, No Drawings

COMPOSITION AND METHOD FOR TREATING KERATIN FIBERS WITH FLASH EVAPORATION

FIELD OF THE INVENTION

The present invention generally relates to the technical field of dyeing of keratin-containing fibers, in particular human hair. The subject matter of the application is specific hair cosmetic formulations which are suitable for application to keratin-containing fibers by means of a flash evaporation method. Additionally, the use of these hair-cosmetic formulations in devices for flash evaporation and methods for temporarily re-shaping keratin-containing fibers are the subject matter of the present invention.

BACKGROUND OF THE INVENTION

These days, an attractive-looking hairstyle is generally considered an indispensable part of a groomed appearance. In order to achieve such an attractive hairstyle, the hair is subjected to cosmetic treatment methods which range from washing by means of a shampoo to permanent re-shaping by means of chemical/thermal methods, or permanent oxidative color brightening. Time-limited durable direct dyes and oxidation dyes are available for dyeing hair. These hair dyes are generally applied to the hair in the form of liquid or foam preparations. When applying dye preparations, for example brushes or foam dispensers are used as auxiliary.

The foam dispensers include in particular pump sprays or aerosol sprays, with the help of which the cosmetic preparations are sprayed via a valve, either by means of mechanical force effect or with the help of a propellant. Both methods have obvious disadvantages. Whereas pump sprays are generally not suitable for a long-lasting uniform spray application of hair-cosmetic preparations, aerosol sprays are based on the use of propellants or gas propellants which, on the one hand, do not display any cosmetic effect and from which, on the other hand, when handled incorrectly, can put a user at risk.

Faced with this background, there is a requirement for alternative ways of spraying or foaming hair-cosmetic preparations. Flash evaporation has proved to be one such alternative spraying method. In this method, which is described for example in international patent application WO 200183071 A1 (Henkel), a liquid or pasty composition including a solvent is heated in a sealed space to a temperature which is above the flash point of the solvent, whereby an above-atmospheric pressure is produced in the composition. When depressurizing (throttling). the liquid vaporizes and can then be sprayed for example by means of a suitable nozzle.

Even if the flash evaporation is thus suitable in principle for spray application of hair-cosmetic preparations, at the same time not every hair-cosmetic preparation can be sprayed by means of a flash evaporation method. On the one hand this is due to the heating of the cosmetic preparation which is required for flash evaporation, and on the other hand the specifics of the spray created by flash evaporation, for example the size and density of the droplets created, in the spray.

Therefore, it is desirable to make available specific hair-cosmetic preparations for dyeing keratin-containing fibers, which preparations, because of their chemical and physical properties, are suitable for precise spray application by means of a device for flash evaporation. Furthermore, the preparations should be suitable for achieving a good cosmetic effect after application by means of a flash evaporation method. Furthermore, other desirable features and characteristics of the present invention will become apparent from the subsequent detailed description of the invention and the appended claims, taken in conjunction with this background of the invention.

BRIEF SUMMARY OF THE INVENTION

A first subject matter of the present invention is thus a cosmetic product, comprising
a) a cosmetic preparation, including, in relation to the total weight thereof
   a1) 50 to 90 wt. % polar solvent; and
   a2) 0.001 to 10 wt. % direct dye, and
b) a device for flash evaporation of the cosmetic preparation a).

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

To achieve this object it has been shown that, from the plurality of preparations which are known to be effective in hair cosmetics, in particular those preparations including solvent are suitable which have specific percentages by weight of direct dyes.

The cosmetic preparation a) is preferably liquid. The cosmetic preparation a) can be present as solution or dispersion, for example as emulsion or suspension. Preferred cosmetic preparations a) are present in the form of a solution or a suspension.

The cosmetic preparation according to the invention includes, as first essential constituent, 50 to 90 wt. % of at least one polar solvent a1). Preferred cosmetic products are characterized in that the percentage by weight of the polar solvent a1) in the total weight of the cosmetic preparation a) is 55 to 85 wt. %, preferably 60 to 80 wt. % and in particular 65 to 75 wt. %. Corresponding agents are characterized by a good cosmetic effect while at the same time possessing good applicability.

To improve the application properties of cosmetic preparations according to the invention while at the same time minimizing the thermal stress of possible active ingredients or auxiliaries in the course of the flash evaporation method, it has proved advantageous to use polar solvents a1) which have a boiling point (20° C., 1013 mbar) of between 50 and 110° C., preferably between 70 and 105° C. Particularly suitable for this have proven to be ethanol, isopropanol and water, which for this reason are preferred as polar solvent a1).

Particularly preferred polar solvents a1) or solvent systems are characterized in that the percentage by weight of water in the total weight of the polar solvent a1) is more than 80 wt. %, preferably more than 85 wt. % and in particular more than 90 wt. %.

A second essential constituent of the cosmetic compositions according to the invention is the direct dye a2). For production and storage, and for the cosmetic properties of the cosmetic preparation a), it has proved advantageous if the percentage by weight of the direct dye a2) in the total weight of the cosmetic preparation a) is 0.002 to 5.0 wt. %, preferably 0.003 to 3.0 wt. %.

Direct dyes can be divided into anionic, cationic and non-ionic direct dyes. The direct dyes are preferably selected from nitrophenylene diamines, nitro amino phenols, azo dyes, anthraquinones or indophenols and the physiologically compatible salts thereof.

In a preferred embodiment, an anionic dye is used as direct dye a2). There are suitable as anionic direct dyes in particular 2,4-Dinitro-1-naphthol-7-sulfonic acid disodium salt (C.I. 10,316; Acid Yellow 1; Food Yellow No. 1), 2-(Indane-1,3-dione-2-yl)quinoline-x,x-sulfonic acid (mixture of mono- and disulfonic acid) (C.I. 47,005; D&C Yellow No. 10; Food Yellow No. 13; Acid Yellow 3, Yellow 10), 5-Hydroxy-1-(4-sulfophenyl)-4-[(4-sulfophenyl)azo] pyrazol-3-carboxylic acid trisodium salt (C.I. 19,140; Food Yellow No. 4; Acid Yellow 23), 3-[(4-Phenylamino)phenyl] azoThenzenesulfonic acid sodium salt (C.I. 13,065; Ki406; Acid Yellow 36), 4-[(2-Hydroxynaphth-1-yl)azo]-benzenesulfonic acid sodium salt (C.I. 15,510; Acid Orange 7), 6-Hydroxy-5-[(4-sulfonaphth-1-yl)azo]-2,4-naphthaline disulfonic acid trisodium salt (C.I. 16,255; Ponceau 4R; Acid Red 18), 8-Amino-1-hydroxy-2-(phenylazo)-3,6-naphthaline disulfonic acid disodium salt (C.I. 17,200; Acid Red 33; Red 33), N-[6-(Diethylamino)-9-(2,4-disulfophenyl)-3H-xanthene-3-ylidene]-N-ethylethane ammonium hydroxide, internal salt, sodium salt (C.I. 45,100; Acid Red 52), 2',4',5',7'-Tetrabromo-4,5,6,7-tetrachloro-3',6'-dihydroxyspiro[isobenzofuran-1(3H),9'[9H]xanthene]-3-one disodium salt (C.I. 45,410; Acid Red 92), 3-Hydroxy-4-[(4-methyl-2-sulfonphenyl)azo]-2-naphthaline carboxylic acid calcium salt (C.I. 15,850:1; Pigment Red 57:1), 1,4-Bis[(2-sulfo-4-methylphenyl)amino]-9,10-anthraquinone disodium salt (C.I. 61,570; Acid Green 25), Bis[4-(dimethylamino) phenyl]-(3,7-disulfo-2-hydroxynaphth-1-yl)carbenium internal salt, sodium salt (C.I. 44,090; Food Green No. 4; Acid Green 50), N-[4-[(2,4-Disulfophenyl)[4-[ethyl(phenylmethyl)amino)phenyl]methylene]-2,5-cyclohexadiene-1-ylidene]-N-ethylbenzolmethanaminium hydroxide, internal salt, sodium salt (C.I. 42,080; Acid Blue 7), (2-Sulfophenyl) di[4-(ethyl((4-sulfophenyl)methyl)amino)phenyl]-carbenium disodium salt betaine (C.I. 42,090; Acid Blue 9; FD&C Blue No. 1), 1-Amino-4-(cyclohexylamino)-9,10-anthraquinone-2-sulfonic acid sodium salt (C.I. 62045; Acid Blue 62), 1-Hydroxy-4-[(4-methyl-2-sulfophenyl)amino]-9,10-anthraquinone sodium salt (C.I. 60,730; D&C Violet No. 2; Acid Violet 43), 5-Amino-4-hydroxy-6-[(4-nitrophenyl)-azo]-3-(phenylazo)-2,7-naphthaline disulfonic acid disodium salt (C.I. 20,470; Acid Black 1), 3-Hydroxy-4-[(2-hydroxynaphth-1-yl)azo]-7-nitro-1-naphthaline sulfonic acid chrome complex (3:2) (C.I. 15,711; Acid Black 52), 3',3'',4,5,5',5'',6,7-Octa-bromophenolsulfonephthalein (Tetrabromophenol blue).

Preferred anionic direct dyes are those compounds known under the international names or trade names Acid Yellow 1, Acid Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1 and Acid Black 52.

In an alternative embodiment a cationic dye is used as direct dye a2). In particular there are suitable as cationic direct dyes Di[4-(diethylamino)phenyl][4-(ethylamino) naphthyl]carbenium chloride (C.I. 42,595; Basic Blue 7), Di[4-(dimethylamino)phenyl][4-(phenylamino)naphthyl] carbenium chloride (C.I. 44,045; Basic Blue 26), 8-Amino-2-bromo-5-hydroxy-4-imino-6-[(3-(trimethylammonio)phenyl)amino]-1(4H)-naphthalinone chloride (C.I. 56,059; Basic Blue No. 99), Tri(4-amino-3-methylphenyl)carbenium chloride (C.I. 42,520; Basic Violet 2), Di(4-aminophenyl)(4-amino-3-methylphenyl)carbenium chloride (C.I. 42,510 Basic Violet 14), 1-[(4-Aminophenyl)azo]-7-(trimethylammonio)-2-naphthol chloride (C.I. 12,250; Basic Brown 16), 1-[(4-Amino-3-nitrophenyl)azo]-7-(trimethylammonio)-2-naphthol chloride (C.I. 12,251; Basic Brown 17), 3-[(4-Amino-2,5-dimethoxyphenyl)azo]-N,N,N-trimethylbenzolammonium chloride (C.I. 12,605, Basic Orange 69), 2-[((4-Dimethylamino)phenyl)azo]-1,3-dimethyl-1H-imidazolium chloride (Basic Red 51), 2-Hydroxy-1-[(2-methoxyphenyl)azo]-7-(trimethylammonio)-naphthalin chloride (C.I. 12,245; Basic Red 76), 2-[4-Aminophenyl] azo]-1,3-dimethyl-1H-imidazolium chloride (Basic Orange 31), 3-Methyl-1-phenyl-4-[(3-(trimethylammonio)phenyl) azo]-pyrazol-5-one chloride (C.I. 12,719; Basic Yellow 57), 1-Methyl-4-((methylphenylhydrazono)methyl)-pyridinium methylsulfate (Basic Yellow 87), 1-(2-Morpholiniumpropylamino)-4-hydroxy-9,10-anthraquinone methylsulfate, 4-Formyl-1-methylquinolonium-p-toluene sulfonate and direct dyes which contain a heterocycle which has at least one quaternary nitrogen atom.

In a further embodiment, a non-ionic dye is used as direct dye a2). In particular, non-ionic nitro dyes and quinone dyes and neutral azo dyes are suitable as non-ionic direct dyes.

Suitable blue nitro dyes are in particular 1,4-Bis[(2-hydroxyethyl)amino]-2-nitrobenzene (HC Violet BS), 1-(2-Hydroxyethyl)amino-2-nitro-4-[di(2-hydroxyethyl)amino]-benzene (HC Blue 2), 4-[Di(2-hydroxyethyl)amino]-1-[(2-methoxyethyl)amino]-2-nitrobenzene (HC Blue 11), 4-[Ethyl-(2-hydroxyethyl)-amino]-1-[(2-hydroxyethyl) amino]-2-nitrobenzene hydrochloride (HC Blue 12), 1-(2-Hydroxyethyl)amino-2-nitro-4-N-ethyl-N-(2-hydroxyethyl) aminobenzene (HC Blue 15), 1-Amino-3-methyl-4-[(2-hydroxyethyl)amino]-6-nitrobenzene (HC Violet 1), 1-(3-Hydroxypropylamino)-4-[di(2-hydroxyethyl)amino]-2-nitrobenzene (HC Violet 2).

Suitable red nitro dyes are in particular 1-Amino-4-[(2-hydroxyethyl)amino]-2-nitrobenzene (HC Red 7), 2-Amino-4,6-dinitrophenol (picramic acid) and the salts thereof, 1,4-Diamino-2-nitrobenzene (C.I. 76,070), 4-Amino-2-nitrodiphenylamine (HC Red 1), 1-Amino-4-[di(2-hydroxyethyl) amino]-2-nitrobenzene hydrochloride (HC Red 13), 1-Amino-4-[(2-hydroxyethyl)-amino]-5-chloro-2-nitrobenzene, 4-Amino-1-[(2-hydroxyethyl)amino]-2-nitrobenzene (HC Red 3), 4-[(2-Hydroxyethyl)-amino]-3-nitrotoluene, 4-Amino-3-nitrophenol, 4-[(2-Hydroxyethyl)-amino]-3-nitrophenol, 4-[(2-Nitrophenyl)amino]phenol (HC Orange 1), 1-[(2-Aminoethyl)amino]-4-(2-hydroxyethoxy)-2-nitrobenzene (HC Orange 2), 1-Amino-5-chloro-4-[(2,3-dihydroxypropyl)amino]-2-nitrobenzene (HC Red 10), 5-Chloro-1,4-[di(2,3-dihydroxypropyl)amino]-2-nitrobenzene (HC Red 11), 2-[(2-Hydroxyethyl)amino]-4,6-dinitrophenol and the salts thereof, 4-Ethylamino-3-nitrobenzoic acid, 2-[(4-Amino-2-nitrophenyl)amino]-benzoic acid, 2-Chloro-6-ethylamino-4-nitrophenol, 2-Amino-6-chloro-4-nitrophenol, 4-[(3-Hydroxypropyl)amino]-3-nitrophenol (HC Red BN), 1,2,3,4-Tetrahydro-6-nitroquinoxaline, 6-Hydroxy-5-((2-methoxy-5-methyl-4-sulfophenyl)azo)-2-naphthalene sulfonic acid (Curry Red).

Suitable yellow nitro dyes are in particular 1,2-Diamino-4-nitrobenzene (C.I. 76,020), 1-[(2-Hydroxyethyl)amino]-2-nitrobenzene (HC Yellow 2), 1-(2-Hydroxyethoxy)-2-[(2-hydroxyethyl)amino]-5-nitrobenzene (HC Yellow 4), 1-Amino-2-[(2-hydroxyethyl)amino]-5-nitrobenzene (HC Yellow 5), 4-[(2,3-Dihydroxypropyl)-amino]-3-nitro-1-trifluormethyl-benzene (HC Yellow 6), 2-[(2-Hydroxyethyl)

amino]-1-methoxy-5-nitrobenzene, 2-Amino-4-nitrophenol, 1-(2-Hydroxyethoxy)-3-methylamino-4-nitrobenzene, 2,3-(Dihydroxypropoxy)-3-methylamino-4-nitrobenzene, 3-[(2-Aminoethyl)amino]-1-methoxy-4-nitrobenzene hydrochloride (HC Yellow 9), 1-Chloro-2,4-bis[(2-hydroxyethyl)amino]-5-nitrobenzene (HC Yellow 10), 2-[(2-Hydroxyethyl)amino]-5-nitrophenol (HC Yellow 11), 1-[(2'-Ureidoethyl)amino]-4-nitrobenzene, 1-Amino-4-[(2-aminoethyl)amino]-5-methyl-2-nitrobenzene, 4-[(2-Hydroxyethyl)amino]-3-nitro-1-methylbenzene, 1-Chloro-4-[(2-hydroxyethyl)amino]-3-nitrobenzene (HC Yellow 12), 4-[(2-Hydroxyethyl)amino]-3-nitro-1-trifluormethyl-benzene (HC Yellow 13).

Suitable quinone dyes are in particular 1-[(2-Hydroxyethyl)amino]-4-methylamino-9,10-anthraquinone (C.I. 61,505, Disperse Blue 3), mixtures of 1,4-bis[(2-hydroxyethyl)amino]anthra-9,10-quinone with 1-[(2-hydroxyethyl)amino]-4-[(3-hydroxypropyl)amino]anthra-9,10-quinone and 1,4-bis[(3-hydroxypropyl)amino]anthra-9,10-quinone (Disperse Blue 377), 1,4-Diamino-9,10-anthraquinone (C.I. 61,100, Disperse Violet 1), 1-Amino-4-(methylamino)-9,10-anthraquinone (C.I. 61,105, Disperse Violet 4, Solvent Violet No. 12), 2-Hydroxy-1,4-naphthoquinone (Lawsone, C.I. 75,480, Natural Orange 6), 1,4-bis[(2,3-dihydroxypropyl)amino]-9,10-anthracenedione (HC Blue 14).

Suitable neutral azo dyes are in particular 1-[Di(2-hydroxyethyl)amino]-3-methyl-4-[(4-nitrophenyl)azo]-benzene (C.I. 11,210, Disperse Red 17), 1-[Di(2-hydroxyethyl)amino]-4-[(4-nitrophenyl)azo]-benzene (Disperse Black 9), 4-[(4-Aminophenyl)azo]-1-[di(2-hydroxyethyl)amino]-3-methylbenzene (HC Yellow 7), 2,6-Diamino-3-[(pyridin-3-yl)azo]-pyridine, 4-[(4-Nitrophenyl)azo]-aniline (C.I. 11,005; Disperse Orange 3).

In addition to the cosmetic preparation a), the cosmetic products according to the invention also comprise a device for flash evaporation. In the scope of the present invention, the expression "flash evaporation" denotes the development of vapor upon a drop in pressure in a closed space filled with a liquid and at above-atmospheric pressure (in respect of the environment). A corresponding above-atmospheric pressure can for example be created by a quantity of the cosmetic preparation a) being heated to a temperature Ti in a closed space. At the given temperature Ti, the liquid has a saturation pressure $p_1$ in the closed space. If the closed space is opened, for example by means of a valve, to a relaxation space with the pressure $p_0 < p_1$ not at above-atmospheric pressure, then the pressure in the previously closed space falls, and in the scope of the new pressure level spreading, the cosmetic preparation a), or the solvent or parts of solvent included in the cosmetic preparation, vaporizes. The resultant vapor or spray can be used for applying specific cosmetic preparations.

If the cosmetic preparation a) is heated in a closed space, thus proceeding from standard conditions ($T_0 = 25°$ C., $p_0 = 1,000$ bar), then, in addition to an increased temperature, an increased pressure in the cosmetic preparation a) also results. This increased pressure can be relieved in a relaxation space to a pressure $p_0$, for example ambient air pressure ($p_0 = 1,000$ bar), whereby at least partially a vaporization of the cosmetic preparation a) is achieved.

The cosmetic preparation a) can be depressurized directly in the space in which it was previously heated. However, the heated, pressurized cosmetic preparation a) can alternatively also be transported into a second space after heating, in which the pressure is then relieved.

In other words, flash evaporation is a method in which the cosmetic preparation a) is heated in a closed container to temperatures above ambient temperature by means of a heating device, wherein a pressure above ambient pressure arises in the container and the heated, pressurized cosmetic preparation a) is then depressurized from the container into the atmosphere.

A device for flash evaporation is, accordingly, a device which comprises a container and a heating device and is designed such that a cosmetic preparation a) can be heated to temperatures above ambient temperature in the closed container in such a way that a pressure above ambient pressure arises in the container and the heated and pressurized cosmetic preparation a) can be depressurized from the container into the environment.

Simultaneously with, or after, the pressure relief, a nozzle can be fitted to the cosmetic preparation a), by means of which for example properties of the vapor or spray created by the flash evaporation, in particular the size or density of the droplets, and also the spray distance and the form of the spraying cone, can be influenced. The use of nozzles, preferably spray nozzles, is therefore preferred. Depending on the respective spray properties, the specific type of nozzle or the specific design of nozzle is then established, in targeted manner.

In summary, a preferred device for flash evaporation has
b1) a container b1) which can be closed and opened by means of a valve, which container defines the closed inner space in which the cosmetic preparation can be received,
b2) a heating device b2) which makes it possible to heat a cosmetic preparation located in the container b1).

The use of an additional nozzle b3) which makes possible a spraying of the cosmetic preparation a) being discharged from the container, is particularly preferred. Alternatively to a valve, also a comparable closing element can be used which can seal or release a respective opening in the container by a corresponding change in position.

A preferred subject matter of the present invention is a cosmetic product, comprising
a) a cosmetic preparation, including, in relation to the total weight thereof
  a1) 50 to 90 wt. % polar solvent;
  a2) 0.001 to 10 wt. % direct dye;
b) a device for flash evaporation of the cosmetic preparation a), wherein the device for flash evaporation comprises a container b1) and a heating device b2) and is designed such that
  the cosmetic preparation a) can be received in the inner space of the container b1),
  the inner space of the container b1) at least partially filled with the cosmetic preparation a) can be sealed,
  the cosmetic preparation a) can be heated in the closed inner space of the container b1) by means of the heating device b2) accompanied by an increase in pressure.

A particularly preferred subject matter of the present invention is therefore a cosmetic product, comprising
a) a cosmetic preparation, including, in relation to the total weight thereof
  a1) 50 to 90 wt. % polar solvent;
  a2) 0.001 to 10 wt. % direct dye;
b) a device for flash evaporation of the cosmetic preparation a), comprising
  b1) a container b1) to be sealed and opened by means of a valve
  b2) a heating device which makes it possible to heat a cosmetic preparation located in the container b1)
  b3) a nozzle b3) which makes possible spraying of the cosmetic preparation a).

In other words, a particularly preferred subject matter of the present invention is a cosmetic product, comprising
a) a cosmetic preparation, including, in relation to the total weight thereof
   a1) 50 to 90 wt. % polar solvent;
   a2) 0.001 to 10 wt. % direct dye;
b) a device for flash evaporation of the cosmetic preparation a), wherein the device for flash evaporation comprises a container b1) and a heating device b2) and is designed such that
   the cosmetic preparation a) can be received in the inner space of the container b1),
   the inner space of the container b1) at least partially filled with the cosmetic preparation a) can be sealed,
   the cosmetic preparation a) can be heated in the closed inner space of the container b1) by means of the heating device b2) accompanied by an increase in pressure,
   the heated cosmetic preparation a) can be depressurized into the environment from the inner space of the container b1) accompanied by a drop in pressure.

The container b1) in which the cosmetic preparation is heated is designed such that it makes it possible for this container to be completely sealed from the environment during heating of the cosmetic preparation a) and, after heating, to be opened to make possible flash evaporation of the cosmetic preparation a). This can for example be ensured by a component for regulating flow control, in particular a valve.

The container b1) in which the cosmetic preparation is heated is preferably in contact with a further container from which the quantity of the cosmetic preparation provided for flash evaporation is transferred before heating in the container b1). The access between this reservoir and container b1) is to be opened and closed via a corresponding device, for example a valve. This further container is preferably designed in the form of a reservoir, which means that it comprises preferably a multiple, for example more than ten times, preferably more than fifty times the quantity of the cosmetic preparation required for a vaporization process. In other words, the other container/reservoir preferably has a multiple, for example more than ten times the volume, preferably more than twenty times and in particular more than fifty times the volume of the container b1).

A further particularly preferred subject matter of the present invention is therefore a cosmetic product, comprising
a) a cosmetic preparation, including, in relation to the total weight thereof
   a1) 50 to 90 wt. % polar solvent;
   a2) 0.001 to 10 wt. % direct dye;
b) a device for flash evaporation of the cosmetic preparation a), comprising
   b1) a container b1) to be sealed and opened by means of a valve;
   b2) a heating device which makes it possible to heat a cosmetic preparation located in the closed container b1);
   b3) a nozzle b3) which makes possible spraying of the cosmetic preparation a);
c) a reservoir for the cosmetic preparation a) from which the cosmetic preparation a) can reach the container b1), wherein
   the access between reservoir and container b1) has a component for regulating flow control, by means of which the flow of the cosmetic preparation a) from the reservoir into the container b1) can be interrupted;
   the reservoir has at least ten times the volume, preferably at least twenty times and in particular at least fifty times the volume of the container b1).

The reservoir is not a pressure vessel and the cosmetic composition located in the reservoir is not pressurized, in other words the pressure inside the reservoir corresponds to ambient pressure (also called air pressure or atmospheric pressure). In this way, corresponding cosmetic products do not for example contain any propellant. Also, the cosmetic product does not have available a pumping device which is suitable for releasing or spraying the cosmetic preparation into the environment without the action of the device for flash evaporation.

A quite particularly preferred subject matter of the present invention is therefore a cosmetic product, comprising
a) a cosmetic preparation, including, in relation to the total weight thereof
   a1) 50 to 90 wt. % polar solvent;
   a2) 0.001 to 10 wt. % direct dye;
b) a device for flash evaporation of the cosmetic preparation a), comprising
   b1) a container b1) to be sealed and opened by means of a valve
   b2) a heating device which makes it possible to heat a cosmetic preparation located in the closed container b1)
   b3) a nozzle b3) which makes possible spraying of the cosmetic preparation a);
c) a reservoir for the cosmetic preparation a) from which the cosmetic preparation a) can reach the container b1), wherein
   the access between reservoir and container b1) has a component for regulating flow control, by means of which the flow of the cosmetic preparation a) from the reservoir into the container b1) can be interrupted;
   the reservoir has at least ten times the volume, preferably at least fifty times the volume of the container b1);
   the pressure inside the reservoir corresponds to ambient pressure.

A quite particularly preferred subject matter of the present invention is therefore a cosmetic product, comprising
a) a cosmetic preparation, including, in relation to the total weight thereof
   a1) 50 to 90 wt. % polar solvent;
   a2) 0.001 to 10 wt. % direct dye;
b) a device for flash evaporation of the cosmetic preparation a), comprising
   b1) a container b1) to be sealed and opened by means of a valve
   b2) a heating device which makes it possible to heat a cosmetic preparation located in the closed container b1)
   b3) a nozzle b3) which makes possible spraying of the cosmetic preparation a);
c) a reservoir for the cosmetic preparation a) from which the cosmetic preparation a) can reach the container b1), wherein
   the access between reservoir and container b1) has a component for regulating flow control, by means of which the flow of the cosmetic preparation a) from the reservoir into the container b1) can be interrupted;
   the reservoir has at least ten times the volume, preferably at least fifty times the volume of the container b1);
   the pressure inside the reservoir corresponds to ambient pressure and the cosmetic product does not contain any propellant.

Furthermore, there are preferred cosmetic products, comprising a) a cosmetic preparation, including, in relation to the total weight thereof
   a1) 50 to 90 wt. % polar solvent;
   a2) 0.001 to 10 wt. % direct dye;
b) a device for flash evaporation of the cosmetic preparation a), comprising
   b1) a container b1) to be sealed and opened by means of a valve
   b2) a heating device which makes it possible to heat a cosmetic preparation located in the closed container b1)
   b3) a nozzle b3) which makes possible spraying of the cosmetic preparation a);
c) a reservoir for the cosmetic preparation a) from which the cosmetic preparation a) can reach the container b1), wherein
   the access between reservoir and container b1) has a component for regulating flow control, by means of which the flow of the cosmetic preparation a) from the reservoir into the container b1) can be interrupted;
   the reservoir has at least ten times the volume, preferably at least fifty times the volume of the container b1);
   the pressure inside the reservoir corresponds to ambient pressure,
wherein the cosmetic product does not have a pumping device which is suitable for releasing or spraying the cosmetic preparation a) without the action of the device for flash evaporation.

In summary, a particularly preferred subject matter of the present invention is therefore a cosmetic product, comprising a) a cosmetic preparation, including, in relation to the total weight thereof
   a1) 50 to 90 wt. % polar solvent;
   a2) 0.001 to 10 wt. % direct dye;
b) a device for flash evaporation of the cosmetic preparation a), comprising
   b1) a container b1) to be sealed and opened by means of a valve;
   b2) a heating device which makes it possible to heat a cosmetic preparation located in the closed container b1);
   b3) a nozzle b3) which makes possible spraying of the cosmetic preparation a);
c) a reservoir for the cosmetic preparation a) from which the cosmetic preparation a) can reach the container b1), wherein
   the access between reservoir and container b1) has a component for regulating flow control, by means of which the flow of the cosmetic preparation a) from the reservoir into the container b1) can be interrupted;
   the reservoir has at least ten times the volume, preferably at least fifty times the volume of the container b1);
   the pressure inside the reservoir corresponds to ambient pressure and the cosmetic product does not contain any propellant,
wherein the cosmetic product does not have a pumping device which is suitable for releasing or spraying the cosmetic preparation a) without the action of the device for flash evaporation.

In addition to the above described constituents a1) and a2), the cosmetic preparations according to the invention can contain a) further active ingredients or auxiliaries, wherein in particular such active ingredients or auxiliaries are preferred which improve the producibility, applicability and/or cosmetic effect of the cosmetic preparations according to the invention.

A first optional constituent of the cosmetic preparations according to the invention is the cationic polymer a3). It has proved advantageous, for the producibility and cosmetic effect of the cosmetic preparation a), if the cosmetic preparation a), in relation to the total weight thereof, includes 0.1 to 5.0 wt. %, preferably 0.2 to 3.0 wt. % and in particular 0.5 to 2.0 wt. % cationic polymer a3).

The group of cationic polymers a3) comprises in particular the cationic polymers with the INCI names Polyquaternium-1, Polyquaternium-2, Polyquaternium-4, Polyquaternium-5, Polyquaternium-6, Polyquaternium-7, Polyquaternium-8, Polyquaternium-9, Polyquaternium-10, Polyquaternium-11, Polyquaternium-12, Polyquaternium-13, Polyquaternium-14, Polyquaternium-15, Polyquaternium-16, Polyquaternium-17, Polyquaternium-18, Polyquaternium-19, Polyquaternium-20, Polyquaternium-22, Polyquaternium-24, Polyquaternium-27, Polyquaternium-28, Polyquaternium-29, Polyquaternium-30, Polyquaternium-31, Polyquaternium-32, Polyquaternium-33, Polyquaternium-34, Polyquaternium-35, Polyquaternium-36, Polyquaternium-39, Polyquaternium-45, Polyquaternium-46, Polyquaternium-47, Polyquaternium-48, Polyquaternium-49, Polyquaternium-50, Polyquaternium-55, Polyquaternium-56, Polyquaternium-68 and Polyquaternium-69.

The zwitterionic surfactants a4), the percentage by weight of which in the total weight of cosmetic preparation is preferably 0.1 to 7.0 wt. %, preferably 0.2 to 5.0 wt. % and in particular 0.5 to 3.0 wt. %, form a second group of optional constituents of the cosmetic preparations a).

Such surface-active compounds which contain at least one quaternary ammonium group and at least one $COO^{(-)}$ or $—SO_3^{(-)}$ group in the molecule are called zwitterionic surfactants and emulsifiers. Particularly suitable zwitterionic surfactants and emulsifiers are the so-called betaines such as N-Alkyl-N,N-dimethylammonium glycinates, for example coco alkyldimethyl ammonium glycinate, N-Acyl-aminopropyl-N,N-dimethyl-ammonium glycinate, for example coco acyl aminopropyl dimethyl ammonium glycinate, and 2-Alkyl-3-carboxymethyl-3-hydroxyethylimidazoline, each with 8 to 18 C atoms in the alkyl or acyl group as well as the coco acyl aminoethyl hydroxyethyl carboxymethyl glycinate. A preferred zwitterionic surfactant is the known fatty acid amide derivative known by the INCI name cocamidopropyl betaine. Cosmetic products, characterized in that the zwitterionic surfactant a4) is selected from the group of substances with the INCI name amidopropyl betaine, preferably from the group of substances with the INCI name cocamidopropyl betaine, are particularly preferred because of their advantageous properties.

Non-ionic surfactants form a third group of preferred optional constituents of the cosmetic preparation. The percentage by weight of the non-ionic surfactants in the total weight of the cosmetic preparation is preferably 0.1 to 6.0 wt. %, preferably 0.2 to 4.0 wt. % and in particular 0.5 to 3.0 wt. %.

Alkylene oxide products of accumulation on saturated linear fatty alcohols, fatty acid esters and fatty acids each with 2 to 80 mol ethylene oxide and/or 1 to 5 mol propylene oxide per mol fatty alcohol or fatty acid have proved to be preferred non-ionic surfactants. Preparations with outstanding properties are likewise obtained if they contain fatty acid esters of ethoxylated glycerol as non-ionic surfactants.

It has proved particularly advantageous if the further non-ionic surfactant has an HLB above 10, preferably above 14. For this it is necessary that the non-ionic surfactant has a sufficiently high degree of ethoxylation.

A further embodiment of the first subject matter of the invention is therefore characterized in that the cosmetic preparation a) includes at least one ethoxylated surfactant with at least 30 ethylene oxide units as non-ionic surfactant.

In addition to the correspondingly ethoxylated fatty alcohols, according to the invention in particular the products of addition of 30 to 60 mol ethylene oxide to castor oil and cured castor oil are particularly suitable. Examples of such suitable surfactants have the INCI names Steareth-30, Ceteareth-30, Oleth-30, Ceteareth-50 or PEG-40 Hydrogenated Castor Oil and PEG-60 Hydrogenated Castor Oil.

The aforementioned ethoxylated non-ionic surfactant(s) can be used in a preferred embodiment also as a mixture with fatty alcohols and/or ionic surfactants in oxidation agent preparation B.

Preferred examples of such mixtures are for example mixtures of fatty alcohols, ethoxylated non-ionic surfactants, in particular ethoxylated cured castor oils and anionic sulfate surfactants. Such a commercial product is offered for example by BASF under the name Emulgade F (INCI name: Cetearyl Alcohol, PEG-40 Castor Oil, Sodium Cetearyl Sulfate).

Cosmetic products, characterized in that the non-ionic surfactant a5) is selected from the group of alkoxylated fatty alcohols, preferably from the group of ethoxylated fatty alcohols, are preferred according to the invention.

A fourth preferred constituent of the cosmetic preparations a) is the anionic surfactant a6). In respect of applicability and cosmetic effect it is preferred if the cosmetic preparation a), in relation to the total weight thereof, includes 0.1 to 6.0 wt. %, preferably 0.2 to 4.0 wt. % and in particular 0.5 to 3.0 wt. % anionic surfactant a6).

Anionic surfactants in the scope of the invention are all anionic surface-active agents suitable for use on the human body. These are characterized by a water-soluble-producing anionic group such as for example a carboxylate, sulfate, sulfonate or phosphate group and a lipophilic alkyl group with, for example, 8 to 30 C atoms. Additionally, glycol or polyglycol ether groups, esters, ethers and amide groups as well as hydroxyl groups can be included in the molecule. Examples of such anionic surfactants are, each in the form of sodium, potassium and ammonium as well as mono-, di- and trialkanol ammonium salts with 2 to 4 C atoms in the alkanol group, linear and branched fatty acids with 8 to 30 C atoms (soaps); ether carboxylic acids, in particular of the formula $RO(CH_2CH_2O)xCH_2COOH$, in which R is a linear alkyl group with 8 to 30 C atoms and x=0 or is 1 to 16; acyl sarcosines; acyl taurines; acyl isethionates; sulfosuccinic acid mono- and dialkylesters as well as sulfosuccinic acid monoalkylpolyoxyethyl esters; linear alkane sulfonates; linear α-olefin sulfonates; sulfonates of unsaturated fatty acids; α-sulfofatty acid methylesters of fatty acids; alkylsulfates and alkylethersulfates, in particular of formula $RO(CH_2CH_2O)_xSO_3H$, in which R stands for a linear alkyl group with 8 to 30 C atoms and x stands for 0 or a number from 1 to 12; mixtures of surface-active hydroxysulfonates; sulfated hydroxyalkyl polyethylene and/or hydroxyalkylene propylene glycol ether; esters of tartaric acid and citric acid with alcohols; alkyl- and/or alkenylether phosphates of formula $RO(C_2H_4O)_xP(=O)(OH)(OR')$, wherein R stands for an aliphatic, optionally unsaturated hydrocarbon residue with 8 to 30 carbon atoms, R' stands for hydrogen, a residue $(CH_2CH_2O)_yR$ and x and y, independently of one another, stands for a number from 1 to 10; sulfated fatty acid alkylene glycol esters of formula $RC(O)O(alkO)_nSO_3H$, in which R stands for a linear or branched, aliphatic, saturated and/or saturated alkyl residue with 6 to 22 C atoms, alk stands for $CH_2CH_2$, $CHCH_3CH_2$ and/or $CH_2CHCH_3$ and n stands for a number from 0.5 to 5; as well as monoglyceride sulfates and monoglyceride ether sulfates.

Preferred anionic surfactants are fatty acids, alkyl sulfates, alkyl ether sulfates and ether carboxylic acids with 10 to 20 C atoms in the alkyl group and up to 16 glycol ether groups in the molecule. Particularly preferred are $C_8$-$C_{20}$ alkyl sulfates, in particular sodium cetearyl sulfate and sodium lauryl sulfate, as well as $C_8$-$C_{20}$ alkyl ether sulfates with 2 to 12, preferably 2 to 4 ethylene oxide groups, in particular sodium lauryl ether sulfate (INCI: Sodium Laureth Sulfate).

The fifth group of particularly preferred optional constituents of the cosmetic preparation a) includes the polyalkylene glycols a7), in particular the polyethylene glycols, the percentage by weight of which in the total weight of the cosmetic preparation is preferably 0.1 to 10 wt. %, preferably 0.5 to 8.0 wt. % and in particular 1.0 to 6.0 wt. %.

Suitable according to the invention are liquid and solid polyethylene glycols (PEG), for example polyalkylene glycols with molar masses of 250 (PEG-4) to 3350 (PEG-75). Particularly preferred are polyethylene glycols with the INCI names PEG-6, PEG-7, PEG-8, PEG-9, PEG-10, PEG-12, PEG-14, PEG-16, PEG-18, PEG-20, PEG-32 and PEG-40. Polyethylene glycols with the INCI name PEG-8 are in particular preferred.

The polymeric thickeners a8) form a last group of particularly preferred constituents of the cosmetic preparation a). Preferred thickeners are selected from the group of polymeric organic thickeners. The polymeric organic thickeners can be cross-linked or non-cross-linked.

In respect of the producibility, applicability and cosmetic effect of cosmetic compositions according to the invention, it has proved advantageous if the percentage by weight of the polymeric thickener a8) in the total weight of the cosmetic preparation a) is 0.1 to 6.0 wt. %, preferably 0.2 to 4.0 wt. % and in particular 0.5 to 2.0 wt. %.

Examples of conventional thickeners a8) are polymeric thickeners with the INCI names Acrylamides Copolymer, Acrylamide/Sodium Acrylate Copolymer, Acrylamide/Sodium Acryloyldimethyltaurate Copolymer, Acrylates/Acetoacetoxyethyl Methacrylate Copolymer, Acrylic Acid/Acrylonitrogens Copolymer, Agar, Agarose, Alcaligenes Polysaccharides, Algin, Alginic Acid, Ammonium Acrylates/Acrylonitrogens Copolymer, Ammonium Acrylates Copolymer, Ammonium Acryloyldimethyltaurate/Vinyl Formamide Copolymer, Ammonium Acryloyldimethyltaurate/VP Copolymer, Ammonium Alginate, Ammonium Polyacryloyldimethyl Taurate, Amylopectin, Ascorbyl Methylsilanol Pectinate, Astragalus Gummifer Gum, Attapulgite, Avena Sativa (Oat) Kernel Flour, Bentonite, Butoxy Chitosan, Caesalpinia Spinosa Gum, Calcium Alginate, Calcium Carboxymethyl Cellulose, Calcium Carrageenan, Calcium Potassium Carbomer, Calcium Starch Octenylsuccinate, C20-40 Alkyl Stearate, Carboxybutyl Chitosan, Carboxymethyl Chitin, Carboxymethyl Chitosan, Carboxymethyl Dextran, Carboxymethyl Hydroxyethylcellulose, Carboxymethyl Hydroxypropyl Guar, Cellulose Acetate Propionate Carboxylate, Cellulose Gum, Ceratonia Siliqua Gum, Cetyl Hydroxyethylcellulose, Cholesterol/HDI/Pullulan Copolymer, Cholesteryl Hexyl Dicarbamate Pullulan, Cyamopsis Tetragonoloba (Guar) Gum, Diglycol/CHDM/lsophthalates/SIP Copolymer, Dihydrogenated Tallow Benzylmonium Hectorite, Dimethicone Crosspolymer-2, Dimethicone Propyl PG-Betaine, DMAPA Acrylates/Acrylic Acid/Acrylonitrogens Copolymer, Ethylene/Sodium Acrylate Copolymer, Gelatin, Gellan Gum, Glyceryl Alginate, Glycine Soja (Soybean) Flour, Guar Hydroxypropyltrimonium Chloride, Hectorite, Hydrated Silica, Hydrogenated Potato Starch, Hydroxybutyl Methylcellulose, Hydroxyethyl Acrylate/Sodium Acryloyldimethyl Taurate Copolymer, Hydroxyethylcellulose, Hydroxyethyl Chitosan, Hydroxyethyl Ethylcellulose, Hydroxypropyl cellulose, Hydroxypropyl Chitosan, Hydroxypropyl Ethylenediamine Carbomer, Hydroxypropyl Guar, Hydroxypropyl Methylcellulose, Hydroxypropyl Methylcellulose Stearoxy Ether, Hydroxystearamide MEA, lsobutylene/Sodium Maleate Copolymer, Lithium Magnesium Silicate, Lithium Magnesium Sodium Silicate, Macrocystis Pyrifera (Kelp), Magnesium Alginate, Magnesium Aluminum Silicate, Magnesium Silicate, Magnesium Trisilicate, Methoxy PEG-22/Dodecyl Glycol Copolymer, Methylcellulose, Methyl Ethylcellulose, Methyl Hydroxyethylcellulose, Microcrystalline Cellulose, Montmorillonite, Moroccan Lava Clay, Natto Gum, Nonoxynyl Hydroxyethylcellulose, Octadecene/MA Copolymer, Pectin, PEG-800, PEG-Crosspolymer, PEG-150/Decyl Alcohol/SMDI Copolymer, PEG-175 Diisostearate, PEG-190 Distearate, PEG-15 Glyceryl Tristearate, PEG-140 Glyceryl Tristearate, PEG-240/HDI Copolymer Bis-Decyltetradeceth-20 Ether, PEG-100/IPDI Copolymer, PEG-180/Laureth-50/TMMG Copolymer, PEG-10/Lauryl Dimethicone Crosspolymer, PEG-15/Lauryl Dimethicone Crosspolymer, PEG-2M, PEG-5M, PEG-7M, PEG-9M, PEG-14M, PEG-20M, PEG-23M, PEG-25M, PEG-45M, PEG-65M, PEG-90M, PEG-115M, PEG-160M, PEG-120 Methyl Glucose Trioleate, PEG-180/Octoxynol-40/TMMG Copolymer, PEG-150 Pentaerythrityl Tetrastearate, PEG-4 Rapeseedamide, PEG-150/Stearyl Alcohol/SMDI Copolymer, Polyacrylate-3, Polyacrylic Acid, Polycyclopentadiene, Polyether-1, Polyethylene/lsopropyl Maleate/MA Copolyol, Polymethacrylic Acid, Polyquaternium-52, Polyvinyl Alcohol, Potassium Alginate, Potassium Aluminum Polyacrylate, Potassium Carbomer, Potassium Carrageenan, Potassium Polyacrylate, Potato Starch Modified, PPG-14 Laureth-60 Hexyl Dicarbamate, PPG-14 Laureth-60 lsophoryl Dicarbamate, PPG-14 Palmeth-60 Hexyl Dicarbamate, Propylene Glycol Alginate, PVP/Decene Copolymer, PVP Montmorillonite, Rhizobian Gum, Ricinoleic Acid/Adipic Acid/AEEA Copolymer, Sclerotium Gum, Sodium Acrylate/Acryloyldimethyl Taurate Copolymer, Sodium Acrylates/Acrolein Copolymer, Sodium Acrylates/Acrylonitrogens Copolymer, Sodium Acrylates Copolymer, Sodium AcrylatesNinyl lsodecanoate Crosspolymer, Sodium Acrylate/Vinyl Alcohol Copolymer, Sodium Carbomer, Sodium Carboxymethyl Chitin, Sodium Carboxymethyl Dextran, Sodium Carboxymethyl Beta-Glucan, Sodium Carboxymethyl Starch, Sodium Carrageenan, Sodium Cellulose Sulfate, Sodium Cyclodextrin Sulfate, Sodium Hydroxypropyl Starch Phosphate, Sodium lsooctylene/MA Copolymer, Sodium Magnesium Fluorosilicate, Sodium Polyacrylate, Sodium Polyacrylate Starch, Sodium Polyacryloyldimethyl Taurate, Sodium Polymethacrylate, Sodium Polystyrene Sulfonate, Sodium Silicoaluminate, Sodium Starch Octenylsuccinate, Sodium Stearoxy PG-Hydroxyethylcellulose Sulfonate, Sodium Styrene/Acrylates Copolymer, Sodium Tauride Acrylates/Acrylic Acid/Acrylonitrogens Copolymer, Solanum Tuberosum (Potato) Starch, Starch/Acrylates/Acrylamide Copolymer, Starch Hydroxypropyltrimonium Chloride, Steareth-60 Cetyl Ether, Steareth-100/PEG-136/HDI Copolymer, Sterculia Urens Gum, Synthetic Fluorphlogopite, Tamarindus lndica Seed Gum, Tapioca Starch, TEA-Alginate, TEA-Carbomer, Triticum Vulgare (Wheat) Starch, Tromethamine Acrylates/Acrylonitrogens Copolymer, Tromethamine Magnesium Aluminum Silicate, Welan Gum, Yeast Beta-Glucan, Yeast Polysaccharides, Zea Mays (Corn) Starch.

Polymeric thickeners a8) from the group of acrylic acid homo- and copolymers, preferably from the group of acrylic acid homopolymers, are particularly preferred.

In addition to the previously described ingredients a1), a2) and a3) to a8) the cosmetic agents according to the invention can contain further active ingredients, auxiliaries and care ingredients.

The composition of some particularly preferred cosmetic preparations according to the invention can be seen in the following tables (details in wt. % in relation to the total weight of the cosmetic agent unless otherwise indicated). In respect of further preferred embodiments of these particularly preferred compositions, the same applies as said before, mutatis mutandis, in respect of the cosmetic preparations a) according to the invention.

|  | Formula 1 | Formula 2 | Formula 3 | Formula 4 | Formula 5 |
| --- | --- | --- | --- | --- | --- |
| Polar solvent a1) | 55 to 85 | 60 to 80 | 65 to 75 | 73 | 70 |
| Direct dye a2) | 0.01 to 10 | 0.02 to 5.0 | 0.03 to 3.0 | 1.2 | 2.1 |
| Optional additives | up to 100 | up to 100 | up to 100 | up to 100 | up to 100 |

|  | Formula 6 | Formula 7 | Formula 8 | Formula 9 | Formula 10 |
| --- | --- | --- | --- | --- | --- |
| Polar solvent a1) | 55 to 85 | 60 to 80 | 65 to 75 | 73 | 70 |
| Anionic direct dye a2) | 0.01 to 10 | 0.02 to 5.0 | 0.03 to 3.0 | 1.2 | 2.1 |
| Optional additives | up to 100 | up to 100 | up to 100 | up to 100 | up to 100 |

|  | Formula 11 | Formula 12 | Formula 13 | Formula | Formula 15 |
| --- | --- | --- | --- | --- | --- |
| Polar solvent a1) | 55 to 85 | 60 to 80 | 65 to 75 | 73 | 70 |
| Cationic direct dye a2) | 0.01 to 10 | 0.02 to 5.0 | 0.03 to 3.0 | 1.2 | 2.1 |
| Optional additives | up to 100 | up to 100 | up to 100 | up to 100 | up to 100 |

|  | Formula 16 | Formula 17 | Formula 18 | Formula | Formula 20 |
| --- | --- | --- | --- | --- | --- |
| Polar solvent a1) | 55 to 85 | 60 to 80 | 65 to 75 | 73 | 70 |
| Non-ionic direct dye a2) | 0.01 to 10 | 0.02 to 5.0 | 0.03 to 3.0 | 1.2 | 2.1 |
| Optional additives | up to 100 | up to 100 | up to 100 | up to 100 | up to 100 |

|  | Formula 21 | Formula 22 | Formula 23 | Formula | Formula 25 |
| --- | --- | --- | --- | --- | --- |
| Polar solvent a1) | 55 to 85 | 60 to 80 | 65 to 75 | 73 | 70 |
| Direct dye a2) | 0.01 to 10 | 0.02 to 5.0 | 0.03 to 3.0 | 1.2 | 2.1 |
| Cationic polymer a3) | 0.1 to 5.0 | 0.2 to 3.0 | 0.5 to 2.0 | 1.0 | 1.4 |
| Optional additives | up to 100 | up to 100 | up to 100 | up to 100 | up to 100 |

-continued

|  | Formula 26 | Formula 27 | Formula 28 | Formula | Formula 30 |
|---|---|---|---|---|---|
| Polar solvent a1) | 55 to 85 | 60 to 80 | 65 to 75 | 73 | 70 |
| Anionic direct dye a2) | 0.01 to 10 | 0.02 to 5.0 | 0.03 to 3.0 | 1.2 | 2.1 |
| Cationic polymer a3) | 0.1 to 5.0 | 0.2 to 3.0 | 0.5 to 2.0 | 1.0 | 1.4 |
| Optional additives | up to 100 | up to 100 | up to 100 | up to 100 | up to 100 |

|  | Formula 31 | Formula 32 | Formula 33 | Formula | Formula 35 |
|---|---|---|---|---|---|
| Polar solvent a1) | 55 to 85 | 60 to 80 | 65 to 75 | 73 | 70 |
| Cationic direct dye a2) | 0.01 to 10 | 0.02 to 5.0 | 0.03 to 3.0 | 1.2 | 2.1 |
| Cationic polymer a3) | 0.1 to 5.0 | 0.2 to 3.0 | 0.5 to 2.0 | 1.0 | 1.4 |
| Optional additives | up to 100 | up to 100 | up to 100 | up to 100 | up to 100 |

|  | Formula 36 | Formula 37 | Formula 38 | Formula | Formula 40 |
|---|---|---|---|---|---|
| Polar solvent a1) | 55 to 85 | 60 to 80 | 65 to 75 | 73 | 70 |
| Non-ionic direct dye a2) | 0.01 to 10 | 0.02 to 5.0 | 0.03 to 3.0 | 1.2 | 2.1 |
| Cationic polymer a3) | 0.1 to 5.0 | 0.2 to 3.0 | 0.5 to 2.0 | 1.0 | 1.4 |
| Optional additives | up to 100 | up to 100 | up to 100 | up to 100 | up to 100 |

|  | Formula 41 | Formula 42 | Formula 43 | Formula | Formula 45 |
|---|---|---|---|---|---|
| Polar solvent a1) | 55 to 85 | 60 to 80 | 65 to 75 | 73 | 70 |
| Direct dye a2) | 0.01 to 10 | 0.02 to 5.0 | 0.03 to 3.0 | 1.2 | 2.1 |
| Zwitterionic surfactant | 0.1 to 7.0 | 0.2 to 5.0 | 0.5 to 3.0 | 1.8 | 1.2 |
| Optional additives | up to 100 | up to 100 | up to 100 | up to 100 | up to 100 |

|  | Formula 46 | Formula 47 | Formula 48 | Formula | Formula 50 |
|---|---|---|---|---|---|
| Polar solvent a1) | 55 to 85 | 60 to 80 | 65 to 75 | 73 | 70 |
| Anionic direct dye a2) | 0.01 to 10 | 0.02 to 5.0 | 0.03 to 3.0 | 1.2 | 2.1 |
| Zwitterionic surfactant | 0.1 to 7.0 | 0.2 to 5.0 | 0.5 to 3.0 | 1.8 | 1.2 |
| Optional additives | up to 100 | up to 100 | up to 100 | up to 100 | up to 100 |

|  | Formula 51 | Formula 52 | Formula 53 | Formula | Formula 55 |
|---|---|---|---|---|---|
| Polar solvent a1) | 55 to 85 | 60 to 80 | 65 to 75 | 73 | 70 |
| Cationic direct dye a2) | 0.01 to 10 | 0.02 to 5.0 | 0.03 to 3.0 | 1.2 | 2.1 |
| Zwitterionic surfactant | 0.1 to 7.0 | 0.2 to 5.0 | 0.5 to 3.0 | 1.8 | 1.2 |
| Optional additives | up to 100 | up to 100 | up to 100 | up to 100 | up to 100 |

|  | Formula 56 | Formula 57 | Formula 58 | Formula | Formula 60 |
|---|---|---|---|---|---|
| Polar solvent a1) | 55 to 85 | 60 to 80 | 65 to 75 | 73 | 70 |
| Non-ionic direct dye a2) | 0.01 to 10 | 0.02 to 5.0 | 0.03 to 3.0 | 1.2 | 2.1 |
| Zwitterionic surfactant | 0.1 to 7.0 | 0.2 to 5.0 | 0.5 to 3.0 | 1.8 | 1.2 |
| Optional additives | up to 100 | up to 100 | up to 100 | up to 100 | up to 100 |

|  | Formula 61 | Formula 62 | Formula 63 | Formula | Formula 65 |
|---|---|---|---|---|---|
| Polar solvent a1) | 55 to 85 | 60 to 80 | 65 to 75 | 73 | 70 |
| Direct dye a2) | 0.01 to 10 | 0.02 to 5.0 | 0.03 to 3.0 | 1.2 | 2.1 |
| Non-ionic surfactant a5) | 0.1 to 6.0 | 0.2 to 4.0 | 0.5 to 3.0 | 1.2 | 1.5 |
| Optional additives | up to 100 | up to 100 | up to 100 | up to 100 | up to 100 |

|  | Formula 66 | Formula 67 | Formula 68 | Formula | Formula 70 |
|---|---|---|---|---|---|
| Polar solvent a1) | 55 to 85 | 60 to 80 | 65 to 75 | 73 | 70 |
| Anionic direct dye a2) | 0.01 to 10 | 0.02 to 5.0 | 0.03 to 3.0 | 1.2 | 2.1 |
| Non-ionic surfactant a5) | 0.1 to 6.0 | 0.2 to 4.0 | 0.5 to 3.0 | 1.2 | 1.5 |
| Optional additives | up to 100 | up to 100 | up to 100 | up to 100 | up to 100 |

|  | Formula 71 | Formula 72 | Formula 73 | Formula | Formula 75 |
|---|---|---|---|---|---|
| Polar solvent a1) | 55 to 85 | 60 to 80 | 65 to 75 | 73 | 70 |
| Cationic direct dye a2) | 0.01 to 10 | 0.02 to 5.0 | 0.03 to 3.0 | 1.2 | 2.1 |
| Non-ionic surfactant a5) | 0.1 to 6.0 | 0.2 to 4.0 | 0.5 to 3.0 | 1.2 | 1.5 |
| Optional additives | up to 100 | up to 100 | up to 100 | up to 100 | up to 100 |

|  | Formula 76 | Formula 77 | Formula 78 | Formula | Formula 80 |
|---|---|---|---|---|---|
| Polar solvent a1) | 55 to 85 | 60 to 80 | 65 to 75 | 73 | 70 |
| Non-ionic direct dye a2) | 0.01 to 10 | 0.02 to 5.0 | 0.03 to 3.0 | 1.2 | 2.1 |
| Non-ionic surfactant a5) | 0.1 to 6.0 | 0.2 to 4.0 | 0.5 to 3.0 | 1.2 | 1.5 |
| Optional additives | up to 100 | up to 100 | up to 100 | up to 100 | up to 100 |

-continued

|  | Formula 81 | Formula 82 | Formula 83 | Formula | Formula 85 |
|---|---|---|---|---|---|
| Polar solvent a1) | 55 to 85 | 60 to 80 | 65 to 75 | 73 | 70 |
| Direct dye a2) | 0.01 to 10 | 0.02 to 5.0 | 0.03 to 3.0 | 1.2 | 2.1 |
| Anionic surfactant a6) | 0.1 to 6.0 | 0.2 to 4.0 | 0.5 to 3.0 | 1.2 | 1.5 |
| Optional additives | up to 100 | up to 100 | up to 100 | up to 100 | up to 100 |

|  | Formula 86 | Formula 87 | Formula 88 | Formula | Formula 90 |
|---|---|---|---|---|---|
| Polar solvent a1) | 55 to 85 | 60 to 80 | 65 to 75 | 73 | 70 |
| Anionic direct dye a2) | 0.01 to 10 | 0.02 to 5.0 | 0.03 to 3.0 | 1.2 | 2.1 |
| Anionic surfactant a6) | 0.1 to 6.0 | 0.2 to 4.0 | 0.5 to 3.0 | 1.2 | 1.5 |
| Optional additives | up to 100 | up to 100 | up to 100 | up to 100 | up to 100 |

|  | Formula 91 | Formula 92 | Formula 93 | Formula | Formula 95 |
|---|---|---|---|---|---|
| Polar solvent a1) | 55 to 85 | 60 to 80 | 65 to 75 | 73 | 70 |
| Cationic direct dye a2) | 0.01 to 10 | 0.02 to 5.0 | 0.03 to 3.0 | 1.2 | 2.1 |
| Anionic surfactant a6) | 0.1 to 6.0 | 0.2 to 4.0 | 0.5 to 3.0 | 1.2 | 1.5 |
| Optional additives | up to 100 | up to 100 | up to 100 | up to 100 | up to 100 |

|  | Formula 96 | Formula 97 | Formula 98 | Formula | Formula |
|---|---|---|---|---|---|
| Polar solvent a1) | 55 to 85 | 60 to 80 | 65 to 75 | 73 | 70 |
| Non-ionic direct dye a2) | 0.01 to 10 | 0.02 to 5.0 | 0.03 to 3.0 | 1.2 | 2.1 |
| Anionic surfactant a6) | 0.1 to 6.0 | 0.2 to 4.0 | 0.5 to 3.0 | 1.2 | 1.5 |
| Optional additives | up to 100 | up to 100 | up to 100 | up to 100 | up to 100 |

|  | Formula | Formula | Formula | Formula | Formula |
|---|---|---|---|---|---|
| Polar solvent a1) | 55 to 85 | 60 to 80 | 65 to 75 | 73 | 70 |
| Direct dye a2) | 0.01 to 10 | 0.02 to 5.0 | 0.03 to 3.0 | 1.2 | 2.1 |
| Polyalkylene glycol a7) | 0.1 to 10 | 0.5 to 8.0 | 1.0 to 6.0 | 4.0 | 5.0 |
| Optional additives | up to 100 | up to 100 | up to 100 | up to 100 | up to 100 |

|  | Formula | Formula | Formula | Formula | Formula |
|---|---|---|---|---|---|
| Polar solvent a1) | 55 to 85 | 60 to 80 | 65 to 75 | 73 | 70 |
| Anionic direct dye a2) | 0.01 to 10 | 0.02 to 5.0 | 0.03 to 3.0 | 1.2 | 2.1 |
| Polyalkylene glycol a7) | 0.1 to 10 | 0.5 to 8.0 | 1.0 to 6.0 | 4.0 | 5.0 |
| Optional additives | up to 100 | up to 100 | up to 100 | up to 100 | up to 100 |

|  | Formula | Formula | Formula | Formula | Formula |
|---|---|---|---|---|---|
| Polar solvent a1) | 55 to 85 | 60 to 80 | 65 to 75 | 73 | 70 |
| Cationic direct dye a2) | 0.01 to 10 | 0.02 to 5.0 | 0.03 to 3.0 | 1.2 | 2.1 |
| Polyalkylene glycol a7) | 0.1 to 10 | 0.5 to 8.0 | 1.0 to 6.0 | 4.0 | 5.0 |
| Optional additives | up to 100 | up to 100 | up to 100 | up to 100 | up to 100 |

|  | Formula | Formula | Formula | Formula | Formula |
|---|---|---|---|---|---|
| Polar solvent a1) | 55 to 85 | 60 to 80 | 65 to 75 | 73 | 70 |
| Non-ionic direct dye a2) | 0.01 to 10 | 0.02 to 5.0 | 0.03 to 3.0 | 1.2 | 2.1 |
| Polyalkylene glycol a7) | 0.1 to 10 | 0.5 to 8.0 | 1.0 to 6.0 | 4.0 | 5.0 |
| Optional additives | up to 100 | up to 100 | up to 100 | up to 100 | up to 100 |

|  | Formula | Formula | Formula | Formula | Formula |
|---|---|---|---|---|---|
| Polar solvent a1) | 55 to 85 | 60 to 80 | 65 to 75 | 73 | 70 |
| Direct dye a2) | 0.01 to 10 | 0.02 to 5.0 | 0.03 to 3.0 | 1.2 | 2.1 |
| Cationic polymer a3) | 0.1 to 5.0 | 0.2 to 3.0 | 0.5 to 2.0 | 1.0 | 1.4 |
| Zwitterionic surfactant | 0.1 to 7.0 | 0.2 to 5.0 | 0.5 to 3.0 | 1.8 | 1.2 |
| Non-ionic surfactant a5) | 0.1 to 6.0 | 0.2 to 4.0 | 0.5 to 3.0 | 1.2 | 1.5 |
| Anionic surfactant a6) | 0.1 to 6.0 | 0.2 to 4.0 | 0.5 to 3.0 | 1.2 | 1.5 |
| Polyalkylene glycol a7) | 0.1 to 10 | 0.5 to 8.0 | 1.0 to 6.0 | 4.0 | 5.0 |
| Thickener a8) | 0.1 to 6.0 | 0.2 to 4.0 | 0.5 to 2.0 | 1.0 | 0.5 |
| Optional additives | up to 100 | up to 100 | up to 100 | up to 100 | up to 100 |

|  | Formula | Formula | Formula | Formula | Formula |
|---|---|---|---|---|---|
| Polar solvent a1) | 55 to 85 | 60 to 80 | 65 to 75 | 73 | 70 |
| Anionic direct dye a2) | 0.01 to 10 | 0.02 to 5.0 | 0.03 to 3.0 | 1.2 | 2.1 |
| Cationic polymer a3) | 0.1 to 5.0 | 0.2 to 3.0 | 0.5 to 2.0 | 1.0 | 1.4 |
| Zwitterionic surfactant | 0.1 to 7.0 | 0.2 to 5.0 | 0.5 to 3.0 | 1.8 | 1.2 |
| Non-ionic surfactant a5) | 0.1 to 6.0 | 0.2 to 4.0 | 0.5 to 3.0 | 1.2 | 1.5 |
| Anionic surfactant a6) | 0.1 to 6.0 | 0.2 to 4.0 | 0.5 to 3.0 | 1.2 | 1.5 |
| Polyalkylene glycol a7) | 0.1 to 10 | 0.5 to 8.0 | 1.0 to 6.0 | 4.0 | 5.0 |

-continued

|  | Formula | Formula | Formula | Formula | Formula |
|---|---|---|---|---|---|
| Thickener a8) | 0.1 to 6.0 | 0.2 to 4.0 | 0.5 to 2.0 | 1.0 | 0.5 |
| Optional additives | up to 100 | up to 100 | up to 100 | up to 100 | up to 100 |

|  | Formula | Formula | Formula | Formula | Formula |
|---|---|---|---|---|---|
| Polar solvent a1) | 55 to 85 | 60 to 80 | 65 to 75 | 73 | 70 |
| Cationic direct dye a2) | 0.01 to 10 | 0.02 to 5.0 | 0.03 to 3.0 | 1.2 | 2.1 |
| Cationic polymer a3) | 0.1 to 5.0 | 0.2 to 3.0 | 0.5 to 2.0 | 1.0 | 1.4 |
| Zwitterionic surfactant | 0.1 to 7.0 | 0.2 to 5.0 | 0.5 to 3.0 | 1.8 | 1.2 |
| Non-ionic surfactant a5) | 0.1 to 6.0 | 0.2 to 4.0 | 0.5 to 3.0 | 1.2 | 1.5 |
| Anionic surfactant a6) | 0.1 to 6.0 | 0.2 to 4.0 | 0.5 to 3.0 | 1.2 | 1.5 |
| Polyalkylene glycol a7) | 0.1 to 10 | 0.5 to 8.0 | 1.0 to 6.0 | 4.0 | 5.0 |
| Thickener a8) | 0.1 to 6.0 | 0.2 to 4.0 | 0.5 to 2.0 | 1.0 | 0.5 |
| Optional additives | up to 100 | up to 100 | up to 100 | up to 100 | up to 100 |

|  | Formula | Formula | Formula | Formula | Formula |
|---|---|---|---|---|---|
| Polar solvent a1) | 55 to 85 | 60 to 80 | 65 to 75 | 73 | 70 |
| Non-ionic direct dye a2) | 0.01 to 10 | 0.02 to 5.0 | 0.03 to 3.0 | 1.2 | 2.1 |
| Cationic polymer a3) | 0.1 to 5.0 | 0.2 to 3.0 | 0.5 to 2.0 | 1.0 | 1.4 |
| Zwitterionic surfactant | 0.1 to 7.0 | 0.2 to 5.0 | 0.5 to 3.0 | 1.8 | 1.2 |
| Non-ionic surfactant a5) | 0.1 to 6.0 | 0.2 to 4.0 | 0.5 to 3.0 | 1.2 | 1.5 |
| Anionic surfactant a6) | 0.1 to 6.0 | 0.2 to 4.0 | 0.5 to 3.0 | 1.2 | 1.5 |
| Polyalkylene glycol a7) | 0.1 to 10 | 0.5 to 8.0 | 1.0 to 6.0 | 4.0 | 5.0 |
| Thickener a8) | 0.1 to 6.0 | 0.2 to 4.0 | 0.5 to 2.0 | 1.0 | 0.5 |
| Optional additives | up to 100 | up to 100 | up to 100 | up to 100 | up to 100 |

|  | Formula | Formula | Formula | Formula | Formula |
|---|---|---|---|---|---|
| Water | 55 to 85 | 60 to 80 | 65 to 75 | 73 | 70 |
| Direct dye a2) | 0.01 to 10 | 0.02 to 5.0 | 0.03 to 3.0 | 1.2 | 2.1 |
| Polyquaternium-6 | 0.1 to 5.0 | 0.2 to 3.0 | 0.5 to 2.0 | 1.0 | 1.4 |
| Cocamidopropyl betaine | 0.1 to 7.0 | 0.2 to 5.0 | 0.5 to 3.0 | 1.8 | 1.2 |
| PEG-40 Castor Oil | 0.1 to 6.0 | 0.2 to 4.0 | 0.5 to 3.0 | 1.2 | 1.5 |
| Sodium lauryl sulfate | 0.1 to 6.0 | 0.2 to 4.0 | 0.5 to 3.0 | 1.2 | 1.5 |
| PEG-8 | 0.1 to 10 | 0.5 to 8.0 | 1.0 to 6.0 | 4.0 | 5.0 |
| Carbomer | 0.1 to 6.0 | 0.2 to 4.0 | 0.5 to 2.0 | 1.0 | 0.5 |
| Optional additives | up to 100 | up to 100 | up to 100 | up to 100 | up to 100 |

|  | Formula | Formula | Formula | Formula | Formula |
|---|---|---|---|---|---|
| Water | 55 to 85 | 60 to 80 | 65 to 75 | 73 | 70 |
| Non-ionic direct dye a2) | 0.01 to 10 | 0.02 to 5.0 | 0.03 to 3.0 | 1.2 | 2.1 |
| Polyquaternium-6 | 0.1 to 5.0 | 0.2 to 3.0 | 0.5 to 2.0 | 1.0 | 1.4 |
| Cocamidopropyl betaine | 0.1 to 7.0 | 0.2 to 5.0 | 0.5 to 3.0 | 1.8 | 1.2 |
| PEG-40 Castor Oil | 0.1 to 6.0 | 0.2 to 4.0 | 0.5 to 3.0 | 1.2 | 1.5 |
| Sodium lauryl sulfate | 0.1 to 6.0 | 0.2 to 4.0 | 0.5 to 3.0 | 1.2 | 1.5 |
| PEG-8 | 0.1 to 10 | 0.5 to 8.0 | 1.0 to 6.0 | 4.0 | 5.0 |
| Carbomer | 0.1 to 6.0 | 0.2 to 4.0 | 0.5 to 2.0 | 1.0 | 0.5 |
| Optional additives | up to 100 | up to 100 | up to 100 | up to 100 | up to 100 |

In addition to the previously described constituents a1) to a6), quite particularly preferred cosmetic preparations contain only small quantities of further active ingredients and auxiliaries. Cosmetic preparations, characterized in that the percentage by weight of the constituents a1), a2) as well as, if present, the optional constituents a3) to a8) in the total weight of the cosmetic preparation is at least 86 wt. %, preferably at least 90 wt. % and in particular at least 94 wt. %, are particularly preferred because of their simple producibility and good cosmetic effect.

As stated at the outset, the cosmetic preparations a) according to the invention are suitable in particular manner for application by means of a device for flash evaporation. A further subject matter of the present invention is therefore the use of a cosmetic preparation a) including, relative to the total weight thereof,
a1) 50 to 90 wt. % polar solvent;
a2) 0.001 to 10 wt. % direct dye;
as process material in a device for flash evaporation.

The subject matter of the present invention is also the use of a product according to the invention for applying a cosmetic preparation a) to keratin-containing fibers, in particular human hair, or for changing the color of keratin-containing fibers, in particular human hair.

A method for changing the color of keratin-containing fibers, in particular human hair, in which a cosmetic preparation a) containing, in relation to the total weight thereof
a1) 50 to 90 wt. % polar solvent;
a2) 0.001 to 10 wt. % direct dye;
is applied to the keratinous fibers by means of a flash evaporation device, forms a further subject matter of the present invention. By means of the flash evaporation device, the cosmetic preparation a) is preferably converted into a spray mist which is then applied to the keratinous fibers.

In order to achieve an adequate spray effect, the cosmetic preparation a) is heated preferably to temperatures above the flash point of the polar solvent or mixture of solvents included in the cosmetic preparation a).

If the polar solvent is water or mixtures of solvent with a water content of above 50 wt. % (in relation to the total weight of the mixture of solvents), the cosmetic preparation is preferably heated to temperatures above 100° C., preferably to temperatures of from 100° C. to 240° C., particularly preferably to temperatures of from 140° C. to 160° C.

In the cases in which the polar solvent is water or mixtures of solvents with a water content above 50 wt. % (in relation to the total weight of the mixture of solvents), the above-atmospheric pressure achieved by heating the cosmetic preparation a) is preferably between 1.1 and 8 bar, preferably between 1.2 and 4 bar.

A preferred subject matter of the application is a method for changing the color of keratinous fibers, in particular human hair, in which a cosmetic preparation a) containing, in relation to the total weight of the preparation,
a1) 50 to 90 wt. % polar solvent;
a2) 0.001 to 10 wt. % direct dye;
is applied to the keratinous fibers by means of a flash evaporation device, wherein
- a partial quantity of the cosmetic preparation located in this reservoir is transferred into a container b1) from a reservoir inside which a pressure obtains which corresponds to ambient pressure;
- subsequently, the access between reservoir and container b1) is interrupted by a component for regulating flow control, by means of which the flow of the cosmetic preparation a) from the reservoir into the container b1) can be interrupted;
- subsequently, the cosmetic preparation a) located in the container b1) sealed against the environment is heated by means of a heating device, with the result that the pressure inside the container b1) increases to values above ambient pressure, preferably to values between 1.1 and 8 bar, in particular to values between 1.2 and 4 bar;
- subsequently, the container b1) pressurized at a pressure above ambient pressure is opened in a manner which makes possible the discharge of at least a partial quantity, preferably at least 50 wt. %, preferably at least 80 wt. % and in particular at least 90 wt. % of the cosmetic preparation located in the container b1), from container b1) into the environment, accompanied by reducing the pressure in the container b1) which obtained at the time the container b1) was opened.

The cosmetic preparation a) is depressurized into the environment, preferably accompanied by the formation of a spray nozzle of the cosmetic preparation a).

The cosmetic preparation a) depressurized from the container b1) is preferably applied to keratin fibers, in particular human hair.

Methods are particularly preferred in the course of which the cosmetic preparation depressurized from the container b1) is guided through a nozzle being applied to the keratinous fibers.

In respect of further preferred embodiments of the uses according to the invention and of the method according to the invention, the same applies as said before, mutatis mutandis, in respect of the cosmetic preparations a) according to the invention and in respect of the device for flash evaporation b).

The agents, uses and methods according to the invention, and some of the preferred embodiments thereof, are characterized in summary by the following points:

A cosmetic product comprising
a) a cosmetic preparation including, relative to the total weight thereof
  a1) 50 to 90 wt. % polar solvent;
  a2) 0.001 to 10 wt. % direct dye;
b) a device for flash evaporation of the cosmetic preparation a).

The cosmetic product according to point 1, characterized in that the device for flash evaporation comprises a container b1) and a heating device b2) and is designed such that
  the cosmetic preparation a) can be received in the inner space of the container b1),
  the inner space of the container b1) at least partially filled with the cosmetic preparation a) can be sealed,
  the cosmetic preparation a) can be heated in the closed inner space of the container b1) by means of the heating device b2) accompanied by an increase in pressure,
  the heated cosmetic preparation a) can be depressurized into the environment from the inner space of the container b1) accompanied by a drop in pressure.

The cosmetic product according to any one of the preceding points, characterized in that the percentage by weight of the polar solvent a1) in the total weight of the cosmetic preparation a) is 55 to 85 wt. %, preferably 60 to 80 wt. % and in particular 65 to 75 wt. %.

The cosmetic product according to any one of the preceding points, characterized in that the polar solvent a1) has a boiling temperature (20° C., 1013 mbar) between 50 and 110° C., preferably between 70 and 105° C.

The cosmetic product according to any one of the preceding points, characterized in that the polar solvent a1) is selected from the group of water and ethanol.

The cosmetic product according to any one of the preceding points, characterized in that the percentage by weight of water in the total weight of the polar solvent a1) is more than 80 wt. %, preferably more than 85 wt. % and in particular more than 90 wt. %.

The cosmetic product according to any one of the preceding points, characterized in that the percentage by weight of the direct dye a2) in the total weight of the cosmetic preparation a) is 0.002 to 5.0 wt. %, preferably 0.003 to 3.0 wt. %.

The cosmetic product according to any one of points 1 to 7. characterized in that a cationic dye is used as direct dye a2).

The cosmetic product according to any one of points 1 to 7. characterized in that an anionic dye is used as direct dye a2).

The cosmetic product according to any one of points 1 to 7. characterized in that a non-ionic dye is used as direct dye a2).

The cosmetic product according to any one of the preceding points, characterized in that, in relation to the total weight thereof, the cosmetic preparation a) includes 0.1 to 5.0 wt. %, preferably 0.2 to 3.0 wt. % and in particular 0.5 to 2.0 wt. % cationic polymer a3).

The cosmetic product according to any one of the preceding points, characterized in that, in relation to the total weight thereof, the cosmetic preparation a) includes 0.1 to 7.0 wt. %, preferably 0.2 to 5.0 wt. % and in particular 0.5 to 3.0 wt. % zwitterionic surfactant a4).

The cosmetic product according to point 12, characterized in that the zwitterionic surfactant a4) is selected from the group of substances with the INCI name amidopropyl betaine, preferably from the group of substances with the INCI name cocamidopropyl betaine.

The cosmetic product according to any one of the preceding points, characterized in that, in relation to the total weight thereof, the cosmetic preparation a) includes 0.1 to 6.0 wt. %, preferably 0.2 to 4.0 wt. % and in particular 0.5 to 3.0 wt. % non-ionic surfactant a5).

The cosmetic product according to point 14, characterized in that the non-ionic surfactant a5) is selected from the group of alkoxylated fatty alcohols, preferably from the group of ethoxylated fatty alcohols.

The cosmetic product according to any one of the preceding points, characterized in that, in relation to the total weight thereof, the cosmetic preparation a) includes 0.1 to 6.0 wt. %, preferably 0.2 to 4.0 wt. % and in particular 0.5 to 3.0 wt. % anionic surfactant a6).

The cosmetic product according to point 16, characterized in that the anionic surfactant a6) is selected from the group of alkyl sulfates and alkyl ether sulfates.

The cosmetic product according to any one of the preceding points, characterized in that, in relation to the total weight thereof, the cosmetic preparation a) includes 0.1 to 10 wt. %, preferably 0.5 to 8.0 wt. % and in particular 1.0 to 6.0 wt. % polyalkylene glycol a7), in particular polyethylene glycol.

The cosmetic product according to any one of the preceding points, characterized in that, in relation to the total weight thereof, the cosmetic preparation a) includes 0.1 to 6.0 wt. %, preferably 0.2 to 4.0 wt. % and in particular 0.5 to 2.0 wt. % of a polymeric thickener a8).

The cosmetic product according to point 19, characterized in that the polymeric thickener a8) is selected from the group of acrylic acid homo- and copolymers, preferably from the group of acrylic acid homopolymers.

The cosmetic product according to any one of the preceding points, characterized in that, in relation to the total weight, thereof, the cosmetic preparation a) consists of at least 86 wt. %, preferably at least 90 wt. % and in particular at least 94 wt. % of constituents a1) and a2) as well as, if present, optional constituents a3) to a8).

A use of a cosmetic preparation a) including, relative to the total weight thereof,
a) a cosmetic preparation including, relative to the total weight thereof
  a1) 50 to 90 wt. % polar solvent;
  a2) 0.001 to 10 wt. % direct dye;
as process material in a device for flash evaporation.

A use of a product according to one any one of points 1 to 21 for applying a cosmetic preparation a) to keratinous fibers, in particular human hair.

A use of a product according to one any one of points 1 to 21 for changing the color of keratin-containing fibers, in particular human hair.

A method for changing the color of keratin-containing fibers, in particular human hair, in which a cosmetic preparation a) including, in relation to the total weight of the preparation,
a1) 50 to 90 wt. % polar solvent;
a2) 0.001 to 10 wt. % direct dye
is applied to the keratinous fibers by means of a flash evaporation device.

The method according to point 25, characterized in that
a partial quantity of the cosmetic preparation a) located in this reservoir is transferred into a container b1) from a reservoir inside which a pressure obtains which corresponds to ambient pressure;
subsequently, the access between reservoir and container b1) is interrupted by a component for regulating flow control, by means of which the flow of the cosmetic preparation a) from the reservoir into the container b1) can be interrupted;
subsequently, the cosmetic preparation a) located in the container b1) sealed against the environment is heated by means of a heating device, with the result that the pressure inside the container b1) increases to values above ambient pressure, preferably to values between 1.1 and 8 bar, in particular to values between 1.2 and 4 bar;
subsequently, the container b1) pressurized at a pressure above ambient pressure is opened in a manner which makes possible the discharge of at least a partial quantity, preferably at least 50 wt. %, preferably at least 80 wt. % and in particular at least 90 wt. % of the cosmetic preparation located in the container b1), from container b1) into the environment, accompanied by reducing the pressure in the container b1) which obtained at the time the container b1) was opened.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A cosmetic product comprising:
   a) a cosmetic preparation comprising, relative to the total weight thereof:
      a1) 50 to 90 wt. % polar solvent, and
      a2) 0.001 to 10 wt. % direct dye; and
   b) a device for flash evaporation of the cosmetic preparation a).

2. The cosmetic product according to claim 1, wherein the device for flash evaporation comprises: a container b1) and a heating device b2), wherein:
   the cosmetic preparation a) can be received in the inner space of the container b1),
   the inner space of the container b1) can be sealed when at least partially filled with the cosmetic preparation a),
   the cosmetic preparation a) can be heated in the closed inner space of the container b1) by means of the heating device b2) accompanied by an increase in pressure, and
   the heated cosmetic preparation a) can be depressurized into the environment from the inner space of the container b1) accompanied by a drop in pressure.

3. The cosmetic product according to claim 1, wherein the polar solvent a1) is 55 to 85 wt. % of the total weight of the cosmetic preparation a).

4. The cosmetic product according to claim 1, wherein the polar solvent a1) is selected from the group consisting of: water, ethanol, and mixtures thereof.

5. The cosmetic product according to claim 1, wherein the direct dye a2) comprises 0.002 to 5.0 wt. % of the total weight of the cosmetic preparation a).

6. The cosmetic product according to claim 1, wherein the cosmetic preparation a) further comprises 0.1 to 5.0 wt. % cationic polymer a3) based on the total weight of the cosmetic preparation a).

7. The cosmetic product according to claim 1, wherein the cosmetic preparation a) further comprises 0.1 to 7.0 wt. % zwitterionic surfactant a4) based on the total weight of the cosmetic preparation a).

8. A method for changing the color of keratin-containing fibers comprising applying a cosmetic preparation a) to the keratin-containing fibers with a flash evaporation device, wherein the cosmetic preparation a) comprises, in relation to the total weight of the preparation:
- a1) 50 to 90 wt. % polar solvent, and
- a2) 0.001 to 10 wt. % direct dye.

9. The method according to claim 8, further comprising:
transferring a partial quantity of the cosmetic preparation a) located in a reservoir into a container b1) of the flash evaporation device, wherein material in the reservoir is at ambient pressure;
reversibly blocking access between the reservoir and the container b1) with a component for regulating flow control;
heating the cosmetic preparation a) located in the container b1), while the container b1 is sealed until a pressure inside the container b1) increases to between 1.1 and 8 bar; and
discharging at least 50 wt. % of the cosmetic preparation from the pressurized container b1) into an environment, the discharged cosmetic preparation contacting the keratin-containing fibers.

10. The method according to claim 9, wherein the cosmetic preparation is heated until the pressure inside the container b1) is between 1.1 and 4 bar.

11. The method according to claim 9, wherein at least 80 wt. % of the cosmetic preparation from the pressurized container b1) is discharged into the environment.

12. The method according to claim 9, wherein the reservoir has a volume at least 50 times the volume of the container b1).

13. The method according to claim 9, further comprising opening access between the reservoir and the container b1) by adjusting the component for regulating flow control.

14. The cosmetic product according to claim 2, wherein the device for flash evaporation further comprises a nozzle.

15. The cosmetic product according to claim 2, wherein the device for flash evaporation further comprises a relaxation space.

16. The cosmetic product according to claim 2, wherein the device for flash evaporation further comprises a valve, wherein the valve seals container b1) during heating.

17. A device for applying a cosmetic product to keratin-containing fibers, the device comprising:
- a heating chamber;
- a reservoir to hold a supply of the cosmetic product;
- a heater to heat cosmetic product in the heating chamber;
- a valve to release heated cosmetic product from the heating chamber such that the released, heated cosmetic product undergoes flash evaporation; and
- a regulator to control movement of cosmetic product between the reservoir and the heating chamber, wherein the cosmetic product comprises:
  - a1) 50 to 90 wt. % polar solvent, and
  - a2) 0.001 to 10 wt. % direct dye, wherein the weight percentages are relative to a total weight of the cosmetic product.

18. The device of claim 17, wherein the device further comprises a nozzle to receive heated cosmetic product from the valve and expel the heated cosmetic product to an environment to contact the keratin-containing fibers.

19. The device of claim 17, wherein the reservoir has a volume at least ten times a volume of the heating chamber.

20. The device of claim 17, wherein the reservoir contains the cosmetic product and the cosmetic product comprises:
- a1) 50 to 90 wt. % polar solvent, and
- a2) 0.001 to 10 wt. % direct dye, wherein the weight percentages are relative to the total weight of the cosmetic product.

* * * * *